US010842219B2

(12) United States Patent
Rowley et al.

(10) Patent No.: US 10,842,219 B2
(45) Date of Patent: Nov. 24, 2020

(54) SMART TOP ROUTES

(71) Applicant: NIKE, Inc., Beaverton, OR (US)

(72) Inventors: Craig Rowley, Beaverton, OR (US); Christopher Andon, Beaverton, OR (US)

(73) Assignee: NIKE, Inc., Beaverton, OR (US)

( * ) Notice: Subject to any disclaimer, the term of this patent is extended or adjusted under 35 U.S.C. 154(b) by 374 days.

(21) Appl. No.: 15/164,315

(22) Filed: May 25, 2016

(65) Prior Publication Data
US 2016/0346611 A1 Dec. 1, 2016

Related U.S. Application Data

(60) Provisional application No. 62/168,504, filed on May 29, 2015.

(51) Int. Cl.
| A63B 24/00 | (2006.01) |
| A43B 3/00 | (2006.01) |
| A61B 5/11 | (2006.01) |
| G01S 19/19 | (2010.01) |
| G06F 19/00 | (2018.01) |
| G06Q 50/00 | (2012.01) |
| G06Q 50/20 | (2012.01) |
| G06Q 30/02 | (2012.01) |
| G01S 19/35 | (2010.01) |

(52) U.S. Cl.
CPC .......... A43B 3/0005 (2013.01); A61B 5/1112 (2013.01); A61B 5/1118 (2013.01); A61B 5/1123 (2013.01); G01S 19/19 (2013.01); G06F 19/3481 (2013.01); G06Q 30/0282 (2013.01); G06Q 50/01 (2013.01); G06Q 50/20 (2013.01); G01S 19/35 (2013.01)

(58) Field of Classification Search
CPC .................................................. A63B 3/0005
See application file for complete search history.

(56) References Cited

U.S. PATENT DOCUMENTS

| 8,649,890 | B2 | 2/2014 | Martin | |
| 9,409,052 | B2* | 8/2016 | Werner | G01S 19/19 |
| 2004/0046692 | A1* | 3/2004 | Robson | A63B 24/0021 342/357.57 |
| 2004/0102931 | A1* | 5/2004 | Ellis | A61B 5/1038 702/188 |
| 2004/0209600 | A1* | 10/2004 | Werner | H01Q 1/273 455/414.1 |
| 2005/0107216 | A1* | 5/2005 | Lee | A63B 24/0084 482/8 |

(Continued)

FOREIGN PATENT DOCUMENTS

| JP | 2013188294 A | 9/2013 |
| WO | 2014144258 A2 | 9/2014 |

OTHER PUBLICATIONS

Aug. 22, 2016—(WO) ISR & WO—App. No. PCT/US16/034101.

Primary Examiner — Tramar Y Harper
(74) Attorney, Agent, or Firm — Banner & Witcoff, Ltd.

(57) ABSTRACT

The disclosure relates to use of athletic data to generate an output, such as for example, running routes and/or other information useful to runners or other workout participants. Aspects of the disclosure further relate to providing customized workouts to runners by generating routes of interest to a user and modifying the generated routes based on goals and external data.

20 Claims, 13 Drawing Sheets

(56) References Cited

U.S. PATENT DOCUMENTS

| | | | |
|---|---|---|---|
| 2006/0136173 A1* | 6/2006 | Case, Jr. | A63B 24/00 |
| | | | 702/182 |
| 2006/0206258 A1* | 9/2006 | Brooks | G01C 21/34 |
| | | | 701/439 |
| 2007/0156335 A1* | 7/2007 | McBride | G01C 21/20 |
| | | | 701/533 |
| 2008/0082254 A1* | 4/2008 | Huhtala | G06F 19/00 |
| | | | 701/533 |
| 2008/0114538 A1* | 5/2008 | Lindroos | G01C 21/26 |
| | | | 701/433 |
| 2010/0216601 A1* | 8/2010 | Saalasti | A61B 5/024 |
| | | | 482/8 |
| 2010/0292050 A1* | 11/2010 | DiBenedetto | A63B 24/0062 |
| | | | 482/9 |
| 2010/0305852 A1* | 12/2010 | Eger | G01C 21/20 |
| | | | 701/533 |
| 2012/0015779 A1* | 1/2012 | Powch | A61B 5/02055 |
| | | | 482/9 |
| 2012/0101717 A1* | 4/2012 | Zhang | G01C 21/20 |
| | | | 701/409 |
| 2012/0259541 A1* | 10/2012 | Downey | G01C 21/20 |
| | | | 701/433 |
| 2013/0231858 A1* | 9/2013 | Bourne | H04W 4/023 |
| | | | 701/439 |
| 2013/0304377 A1* | 11/2013 | Van Hende | G01C 21/20 |
| | | | 701/533 |
| 2013/0345978 A1* | 12/2013 | Lush | G01C 21/00 |
| | | | 701/533 |
| 2014/0303892 A1 | 10/2014 | Morlock | |
| 2016/0135743 A1* | 5/2016 | Cobbett | A61B 5/1118 |
| | | | 600/479 |

* cited by examiner

SMART TOP ROUTES

The application claims priority to provisional U.S. Application No. 62/168,504, which was filed on May 29, 2015, the disclosure and content of which is hereby incorporated by reference in its entirety.

BACKGROUND

While most people appreciate the importance of physical fitness, many have difficulty finding the motivation required to maintain a regular exercise program or to continually improve their workouts during their exercise routines. Moreover, individuals may view exercise as work or a chore and thus, separate it from enjoyable aspects of their daily lives. Often, this separation between athletic activity and other activities reduces the amount of motivation that an individual might have toward exercising. Further, athletic activity services and systems directed toward encouraging individuals to engage in athletic activities might also be too focused on one or more particular activities while an individual's interests are ignored. This may further decrease a user's interest in participating in athletic activities or using the athletic activity services and systems.

Therefore, improved systems and methods to address these and other shortcomings in the art are desired. Exercising

BRIEF DESCRIPTION OF THE DRAWINGS

FIGS. 6A-13 illustrate example interfaces from a route activity tracking device in which route details are displayed according to various aspects of the disclosure.

DETAILED DESCRIPTION

Aspects of this disclosure involve obtaining, storing, and/or processing athletic data relating to the physical movements of an athlete. The athletic data may be actively or passively sensed and/or stored in one or more non-transitory storage mediums. Still further aspects relate to using athletic data to generate an output, such as for example, calculated athletic attributes, feedback signals to provide guidance, and/or other information. Even further aspects relate to motivating and encouraging users to continue exercising or increase exercise intently by engaging them with new and exciting routes to run and encouraging them to reach exercise goals running such routes. These and other aspects will be discussed in the context of the following illustrative examples of a personal training system.

In the following description of the various embodiments, reference is made to the accompanying drawings, which form a part hereof, and in which is shown by way of illustration various embodiments in which aspects of the disclosure may be practiced. It is to be understood that other embodiments may be utilized and structural and functional modifications may be made without departing from the scope and spirit of the present disclosure. Further, headings within this disclosure should not be considered as limiting aspects of the disclosure and the example embodiments are not limited to the example headings.

I. Example Personal Training System

A. Illustrative Networks

Figure 1:
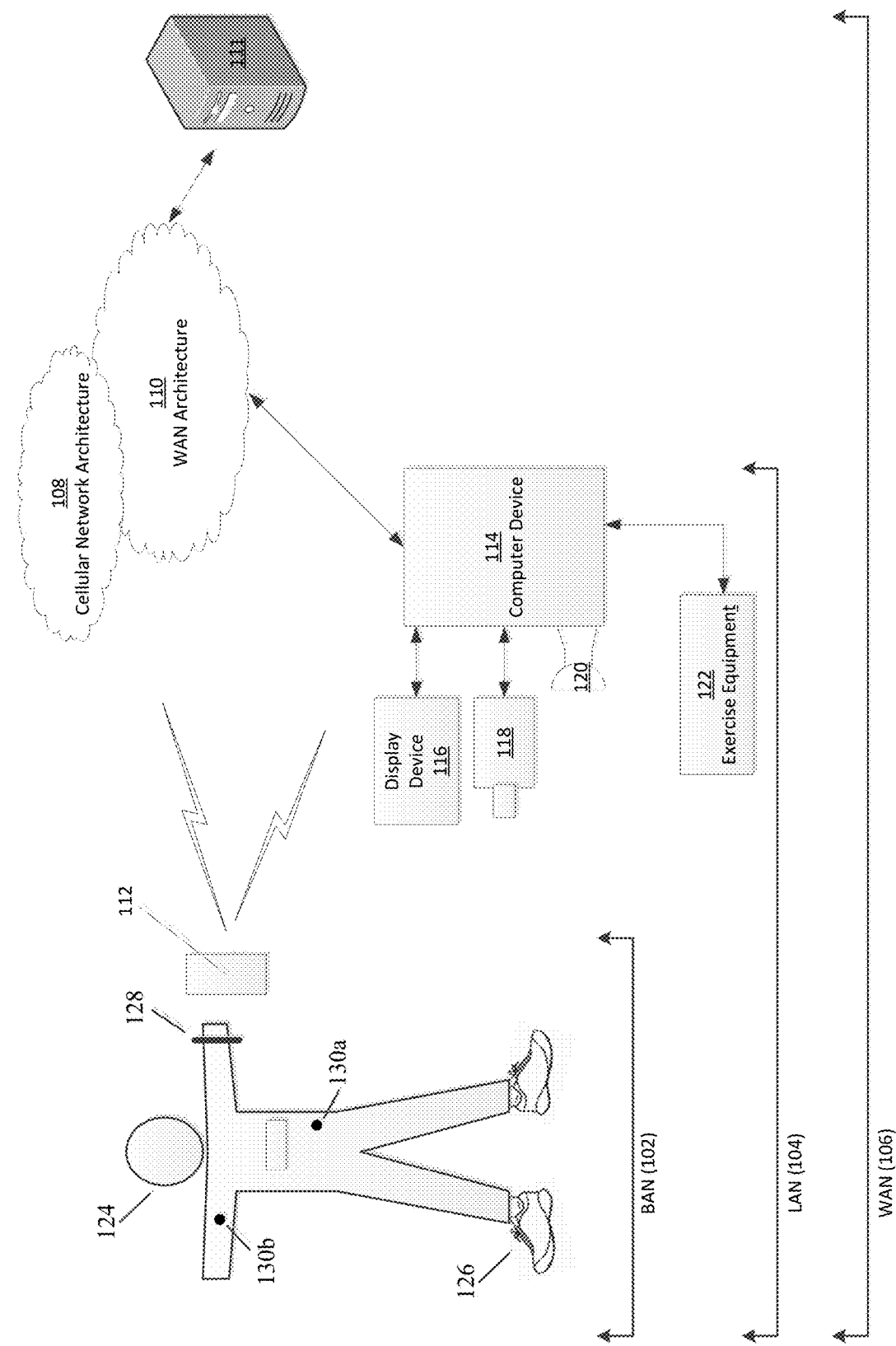
FIG. 1 illustrates an example system that may be configured to provide personal training and/or obtain data from the physical movements of a user in accordance with example embodiments.

Aspects of this disclosure relate to systems and methods that may be utilized across a plurality of networks. In this regard, certain embodiments may be configured to adapt to dynamic network environments. Further embodiments may be operable in differing discrete network environments. FIG. 1 illustrates an example of a personal training system 100 in accordance with example embodiments. Example system 100 may include one or more interconnected networks, such as the illustrative body area network (BAN) 102, local area network (LAN) 104, and wide area network (WAN) 106. As shown in FIG. 1 (and described throughout this disclosure), one or more networks (e.g., BAN 102, LAN 104, and/or WAN 106), may overlap or otherwise be inclusive of each other. Those skilled in the art will appreciate that the illustrative networks 102-106 are logical networks that may each comprise one or more different communication protocols and/or network architectures and yet may be configured to have gateways to each other or other networks. For example, each of BAN 102, LAN 104 and/or WAN 106 may be operatively connected to the same physical network architecture, such as cellular network architecture 108 and/or WAN architecture 110. For example, portable electronic device 112, which may be considered a component of both BAN 102 and LAN 104, may comprise a network adapter or network interface card (NIC) configured to translate data and control signals into and from network messages according to one or more communication protocols, such as the Transmission Control Protocol (TCP), the Internet Protocol (IP), and the User Datagram Protocol (UDP) through one or more of architectures 108 and/or 110. These protocols are well known in the art, and thus will not be discussed here in more detail.

Network architectures 108 and 110 may include one or more information distribution network(s), of any type(s) or topology(s), alone or in combination(s), such as for example, cable, fiber, satellite, telephone, cellular, wireless, etc. and as such, may be variously configured such as having one or more wired or wireless communication channels (including but not limited to: WiFi®, Bluetooth®, Near-Field Communication (NFC) and/or ANT technologies). Thus, any device within a network of FIG. 1, (such as portable electronic device 112 or any other device described herein) may be considered inclusive to one or more of the different logical networks 102-106. With the foregoing in mind, example components of an illustrative BAN and LAN (which may be coupled to WAN 106) will be described.

1. Example Local Area Network

LAN 104 may include one or more electronic devices, such as for example, computer device 114. Computer device 114, or any other component of system 100, may comprise a mobile terminal, such as a telephone, music player, tablet, netbook or any portable device. In other embodiments, computer device 114 may comprise a media player or recorder, desktop computer, server(s), a gaming console, such as for example, a Microsoft® XBOX, Sony® Playstation, and/or a Nintendo® Wii gaming consoles. Those skilled in the art will appreciate that these are merely example devices for descriptive purposes and this disclosure is not limited to any console or computing device.

Figure 2:
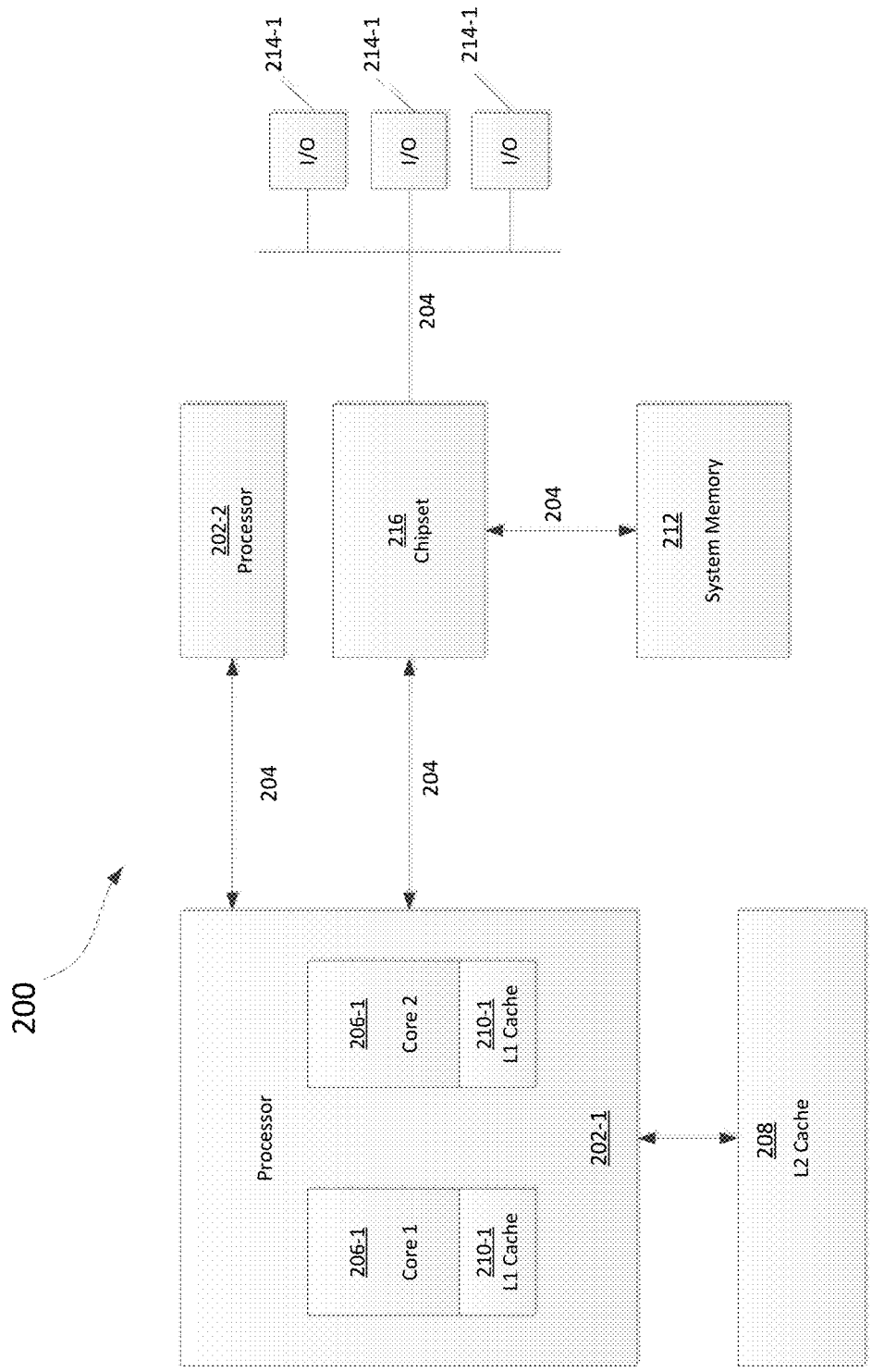
FIG. 2 illustrates an example computer device that may be part of or in communication with the system of FIG. 1.

Those skilled in the art will appreciate that the design and structure of computer device 114 may vary depending on several factors, such as its intended purpose. One example implementation of computer device 114 is provided in FIG. 2, which illustrates a block diagram of computing device 200. Those skilled in the art will appreciate that the disclosure of FIG. 2 may be applicable to any device disclosed herein. Device 200 may include one or more processors, such as processor 202-1 and 202-2 (generally referred to herein as "processors 202" or "processor 202"). Processors 202 may communicate with each other or other components via an interconnection network or bus 204. Processor 202 may include one or more processing cores, such as cores 206-1 and 206-2 (referred to herein as "cores 206" or more generally as "core 206"), which may be implemented on a single integrated circuit (IC) chip.

Cores 206 may comprise a shared cache 208 and/or a private cache (e.g., caches 210-1 and 210-2, respectively). One or more caches 208/210 may locally cache data stored in a system memory, such as memory 212, for faster access by components of the processor 202. Memory 212 may be in communication with the processors 202 via a chipset 216. Cache 208 may be part of system memory 212 in certain embodiments. Memory 212 may include, but is not limited to, random access memory (RAM), read only memory (ROM), and include one or more of solid-state memory, optical or magnetic storage, and/or any other medium that can be used to store electronic information. Yet other embodiments may omit system memory 212.

System 200 may include one or more I/O devices (e.g., I/O devices 214-1 through 214-3, each generally referred to as I/O device 214). I/O data from one or more I/O devices 214 may be stored at one or more caches 208, 210 and/or system memory 212. Each of I/O devices 214 may be permanently or temporarily configured to be in operative communication with a component of system 100 using any physical or wireless communication protocol.

Returning to FIG. 1, four example I/O devices (shown as elements 116-122) are shown as being in communication with computer device 114. Those skilled in the art will appreciate that one or more of devices 116-122 may be stand-alone devices or may be associated with another device besides computer device 114. For example, one or more I/O devices may be associated with or interact with a component of BAN 102 and/or WAN 106. I/O devices 116-122 may include, but are not limited to athletic data acquisition units, such as for example, sensors. One or more I/O devices may be configured to sense, detect, and/or measure an athletic parameter from a user, such as user 124. Examples include, but are not limited to: an accelerometer, a gyroscope, a location-determining device (e.g., GPS), light (including non-visible light) sensor, temperature sensor (including ambient temperature and/or body temperature), sleep pattern sensors, heart rate monitor, image-capturing sensor, moisture sensor, force sensor, compass, angular rate sensor, and/or combinations thereof among others.

In further embodiments, I/O devices 116-122 may be used to provide an output (e.g., audible, visual, or tactile cue) and/or receive an input, such as a user input from athlete 124. Example uses for these illustrative I/O devices are provided below, however, those skilled in the art will appreciate that such discussions are merely descriptive of some of the many options within the scope of this disclosure. Further, reference to any data acquisition unit, I/O device, or sensor is to be interpreted disclosing an embodiment that may have one or more I/O device, data acquisition unit, and/or sensor disclosed herein or known in the art (either individually or in combination).

Information from one or more devices (across one or more networks) may be used to provide (or be utilized in the formation of) a variety of different parameters, metrics or physiological characteristics including but not limited to: motion parameters, such as speed, acceleration, distance, steps taken, direction, relative movement of certain body portions or objects to others, or other motion parameters which may be expressed as angular rates, rectilinear rates or combinations thereof, physiological parameters, such as calories, heart rate, sweat detection, effort, oxygen consumed, oxygen kinetics, and other metrics which may fall within one or more categories, such as: pressure, impact forces, information regarding the athlete, such as height, weight, age, demographic information and combinations thereof.

System 100 may be configured to transmit and/or receive athletic data, including the parameters, metrics, or physiological characteristics collected within system 100 or otherwise provided to system 100. As one example, WAN 106 may comprise server 111. Server 111 may have one or more components of system 200 of FIG. 2. In one embodiment, server 111 comprises at least a processor and a memory, such as processor 206 and memory 212. Server 111 may be configured to store computer-executable instructions on a non-transitory computer-readable medium. The instructions may comprise athletic data, such as raw or processed data collected within system 100. System 100 may be configured to transmit data, such as energy expenditure points, to a social networking website or host such a site. Server 111 may be utilized to permit one or more users to access and/or compare athletic data. As such, server 111 may be configured to transmit and/or receive notifications based upon athletic data or other information.

Returning to LAN 104, computer device 114 is shown in operative communication with a display device 116, an image-capturing device 118, sensor 120 and exercise device 122, which are discussed in turn below with reference to example embodiments. In one embodiment, display device 116 may provide audio-visual cues to athlete 124 to perform a specific athletic movement. The audio-visual cues may be provided in response to computer-executable instruction executed on computer device 114 or any other device, including a device of BAN 102 and/or WAN. Display device 116 may be a touchscreen device or otherwise configured to receive a user-input.

In one embodiment, data may be obtained from image-capturing device 118 and/or other sensors, such as sensor 120, which may be used to detect (and/or measure) athletic parameters, either alone or in combination with other devices, or stored information. Image-capturing device 118 and/or sensor 120 may comprise a transceiver device. In one embodiment sensor 128 may comprise an infrared (IR), electromagnetic (EM) or acoustic transceiver. For example, image-capturing device 118, and/or sensor 120 may transmit waveforms into the environment, including towards the direction of athlete 124 and receive a "reflection" or otherwise detect alterations of those released waveforms. Those skilled in the art will readily appreciate that signals corresponding to a multitude of different data spectrums may be utilized in accordance with various embodiments. In this regard, devices 118 and/or 120 may detect waveforms emitted from external sources (e.g., not system 100). For example, devices 118 and/or 120 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology.

In one embodiment, exercise device 122 may be any device configurable to permit or facilitate the athlete 124 performing a physical movement, such as for example a treadmill, step machine, etc. There is no requirement that the device be stationary. In this regard, wireless technologies permit portable devices to be utilized, thus a bicycle or other mobile exercising device may be utilized in accordance with certain embodiments. Those skilled in the art will appreciate that equipment 122 may be or comprise an interface for receiving an electronic device containing athletic data performed remotely from computer device 114. For example, a user may use a sporting device (described below in relation to BAN 102) and upon returning home or the location of equipment 122, download athletic data into element 122 or any other device of system 100. Any I/O device disclosed herein may be configured to receive activity data.

2. Body Area Network

BAN 102 may include two or more devices configured to receive, transmit, or otherwise facilitate the collection of athletic data (including passive devices). Exemplary devices may include one or more data acquisition units, sensors, or devices known in the art or disclosed herein, including but not limited to I/O devices 116-122. Two or more components of BAN 102 may communicate directly, yet in other embodiments, communication may be conducted via a third device, which may be part of BAN 102, LAN 104, and/or WAN 106. One or more components of LAN 104 or WAN 106 may form part of BAN 102. In certain implementations, whether a device, such as portable device 112, is part of BAN 102, LAN 104, and/or WAN 106, may depend on the athlete's proximity to an access point to permit communication with mobile cellular network architecture 108 and/or WAN architecture 110. User activity and/or preference may also influence whether one or more components are utilized as part of BAN 102. Example embodiments are provided below.

User 124 may be associated with (e.g., possess, carry, wear, and/or interact with) any number of devices, such as portable device 112, shoe-mounted device 126, wrist-worn device 128 and/or a sensing location, such as sensing location 130, which may comprise a physical device or a location that is used to collect information. One or more devices 112, 126, 128, and/or 130 may not be specially designed for fitness or athletic purposes. Indeed, aspects of this disclosure relate to utilizing data from a plurality of devices, some of which are not fitness devices, to collect, detect, and/or measure athletic data. In certain embodiments, one or more devices of BAN 102 (or any other network) may comprise a fitness or sporting device that is specifically designed for a particular sporting use. As used herein, the term "sporting device" includes any physical object that may be used or implicated during a specific sport or fitness activity. Exemplary sporting devices may include, but are not limited to: golf balls, basketballs, baseballs, soccer balls, footballs, powerballs, hockey pucks, weights, bats, clubs, sticks, paddles, mats, and combinations thereof. In further embodiments, exemplary fitness devices may include objects within a sporting environment where a specific sport occurs, including the environment itself, such as a goal net, hoop, backboard, portions of a field, such as a midline, outer boundary marker, base, and combinations thereof.

In this regard, those skilled in the art will appreciate that one or more sporting devices may also be part of (or form) a structure and vice-versa, a structure may comprise one or more sporting devices or be configured to interact with a sporting device. For example, a first structure may comprise a basketball hoop and a backboard, which may be removable and replaced with a goal post. In this regard, one or more sporting devices may comprise one or more sensors, such as one or more of the sensors discussed above in relation to FIGS. 1-3, that may provide information utilized, either independently or in conjunction with other sensors, such as one or more sensors associated with one or more structures. For example, a backboard may comprise a first sensor configured to measure a force and a direction of the force by a basketball upon the backboard and the hoop may comprise a second sensor to detect a force. Similarly, a golf club may comprise a first sensor configured to detect grip attributes on the shaft and a second sensor configured to measure impact with a golf ball.

Looking to the illustrative portable device 112, it may be a multi-purpose electronic device, that for example, includes a telephone or digital music player, including an IPOD®, IPAD®, or iPhone®, brand devices available from Apple, Inc. of Cupertino, Calif. or Zune® or Microsoft® Windows devices available from Microsoft of Redmond, Wash. As known in the art, digital media players can serve as an output device, input device, and/or storage device for a computer. Device 112 may be configured as an input device for receiving raw or processed data collected from one or more devices in BAN 102, LAN 104, or WAN 106. In one or more embodiments, portable device 112 may comprise one or more components of computer device 114. For example, portable device 112 may be include a display 116, image-capturing device 118, and/or one or more data acquisition devices, such as any of the I/O devices 116-122 discussed above, with or without additional components, so as to comprise a mobile terminal.

a. Illustrative Apparel/Accessory Sensors

In certain embodiments, I/O devices may be formed within or otherwise associated with user's 124 clothing or accessories, including a watch, armband, wristband, necklace, shirt, shoe, or the like. These devices may be configured to monitor athletic movements of a user. It is to be understood that they may detect athletic movement during user's 124 interactions with computer device 114 and/or operate independently of computer device 114 (or any other device disclosed herein). For example, one or more devices in BAN 102 may be configured to function as an all-day activity monitor that measures activity regardless of the user's proximity or interactions with computer device 114. It is to be further understood that the sensory system 302 shown in FIG. 3 and the device assembly 400 shown in FIG. 4, each of which are described in the following paragraphs, are merely illustrative examples.

i. Shoe-Mounted Device

Figure 3:
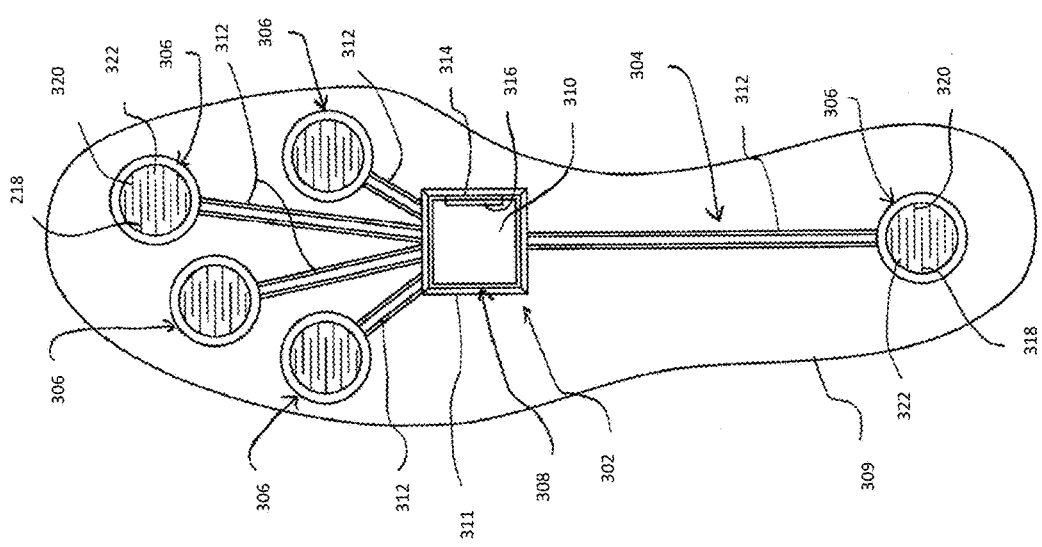
FIG. 3 shows an illustrative sensor assembly that may be worn by a user in accordance with example embodiments.

In certain embodiments, device 126 shown in FIG. 1, may comprise footwear which may include one or more sensors, including but not limited to those disclosed herein and/or known in the art. FIG. 3 illustrates one example embodiment of a sensor system 302 providing one or more sensor assemblies 304. Assembly 304 may comprise one or more sensors, such as for example, an accelerometer, gyroscope, location-determining components, force sensors and/or or any other sensor disclosed herein or known in the art. In the illustrated embodiment, assembly 304 incorporates a plurality of sensors, which may include force-sensitive resistor (FSR) sensors 306; however, other sensor(s) may be utilized. Port 308 may be positioned within a sole structure 309 of a shoe, and is generally configured for communication with one or more electronic devices. Port 308 may optionally be provided to be in communication with an electronic module 310, and the sole structure 309 may optionally include a housing 311 or other structure to receive the module 310. The sensor system 302 may also include a plurality of leads 312 connecting the FSR sensors 306 to the port 308, to enable communication with the module 310 and/or another electronic device through the port 308. Module 310 may be contained within a well or cavity in a sole structure of a shoe, and the housing 311 may be positioned within the well or cavity. In one embodiment, at least one gyroscope and at least one accelerometer are provided within a single housing, such as module 310 and/or housing 311. In at least a further embodiment, one or more sensors are provided that, when operational, are configured to provide directional information and angular rate data. The port 308 and the module 310 include complementary interfaces 314, 316 for connection and communication.

In certain embodiments, at least one force-sensitive resistor 306 shown in FIG. 3 may contain first and second electrodes or electrical contacts 318, 320 and a force-sensitive resistive material 322 disposed between the electrodes 318, 320 to electrically connect the electrodes 318, 320 together. When pressure is applied to the force-sensitive material 322, the resistivity and/or conductivity of the force-sensitive material 322 changes, which changes the electrical potential between the electrodes 318, 320. The change in resistance can be detected by the sensor system 302 to detect the force applied on the sensor 316. The force-sensitive resistive material 322 may change its resistance under pressure in a variety of ways. For example, the force-sensitive material 322 may have an internal resistance that decreases when the material is compressed. Further embodiments may utilize "volume-based resistance", which may be implemented through "smart materials." As another example, the material 322 may change the resistance by changing the degree of surface-to-surface contact, such as between two pieces of the force sensitive material 322 or between the force sensitive material 322 and one or both electrodes 318, 320. In some circumstances, this type of force-sensitive resistive behavior may be described as "contact-based resistance."

ii. Wrist-Worn Device

Figure 4:
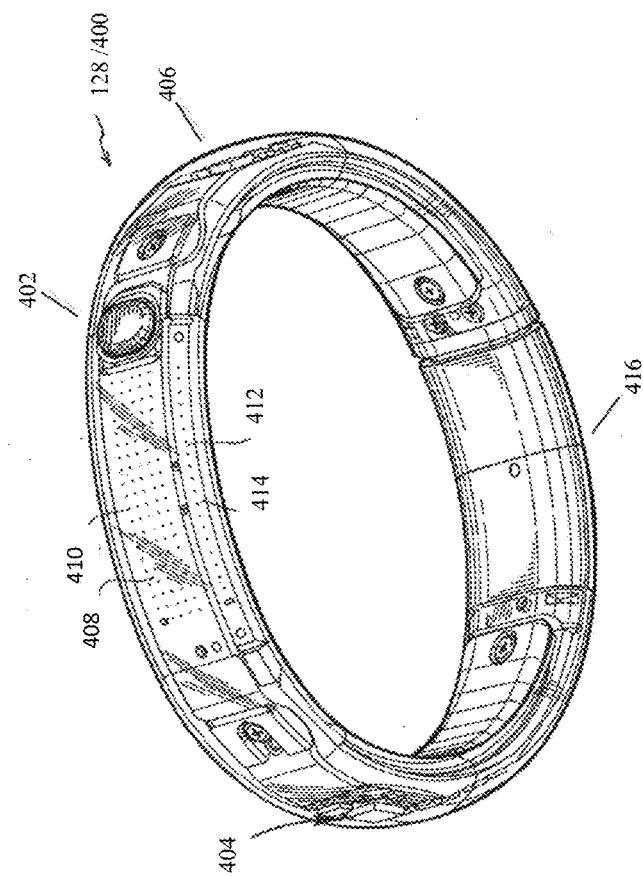
FIG. 4 shows another example sensor assembly that may be worn by a user in accordance with example embodiments.

As shown in FIG. 4, device 400 (which may resemble or comprise sensory device 128 shown in FIG. 1), may be configured to be worn by user 124, such as around a wrist, arm, ankle, neck or the like. Device 400 may include an input mechanism, such as a depressible input button 402 configured to be used during operation of the device 400. The input button 402 may be operably connected to a controller 404 and/or any other electronic components, such as one or more of the elements discussed in relation to computer device 114 shown in FIG. 1. Controller 404 may be embedded or otherwise part of housing 406. Housing 406 may be formed of one or more materials, including elastomeric components and comprise one or more displays, such as display 408. The display may be considered an illuminable portion of the device 400. The display 408 may include a series of individual lighting elements or light members such as LED lights 410. The lights may be formed in an array and operably connected to the controller 404. Device 400 may include an indicator system 412, which may also be considered a portion or component of the overall display 408. Indicator system 412 can operate and illuminate in conjunction with the display 408 (which may have pixel member 414) or completely separate from the display 408. The indicator system 412 may also include a plurality of additional lighting elements or light members, which may also take the form of LED lights in an exemplary embodiment. In certain embodiments, indicator system may provide a visual indication of goals, such as by illuminating a portion of lighting members of indicator system 412 to represent accomplishment towards one or more goals. Device 400 may be configured to display data expressed in terms of activity points or currency earned by the user based on the activity of the user, either through display 408 and/or indicator system 412.

A fastening mechanism 416 can be disengaged wherein the device 400 can be positioned around a wrist or portion of the user 124 and the fastening mechanism 416 can be subsequently placed in an engaged position. In one embodiment, fastening mechanism 416 may comprise an interface, including but not limited to a USB port, for operative interaction with computer device 114 and/or devices, such as devices 120 and/or 112. In certain embodiments, fastening member may comprise one or more magnets. In one embodiment, fastening member may be devoid of moving parts and rely entirely on magnetic forces.

In certain embodiments, device 400 may comprise a sensor assembly (not shown in FIG. 4). The sensor assembly may comprise a plurality of different sensors, including those disclosed herein and/or known in the art. In an example embodiment, the sensor assembly may comprise or permit operative connection to any sensor disclosed herein or known in the art. Device 400 and or its sensor assembly may be configured to receive data obtained from one or more external sensors.

iii. Apparel and/or Body Location Sensing

Element 130 of FIG. 1 shows an example sensory location which may be associated with a physical apparatus, such as a sensor, data acquisition unit, or other device. Yet in other embodiments, it may be a specific location of a body portion or region that is monitored, such as via an image capturing device (e.g., image capturing device 118). In certain embodiments, element 130 may comprise a sensor, such that elements 130a and 130b may be sensors integrated into apparel, such as athletic clothing. Such sensors may be placed at any desired location of the body of user 124. Sensors 130a/b may communicate (e.g., wirelessly) with one or more devices (including other sensors) of BAN 102, LAN 104, and/or WAN 106. In certain embodiments, passive sensing surfaces may reflect waveforms, such as infrared light, emitted by image-capturing device 118 and/or sensor 120. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Figure 5:
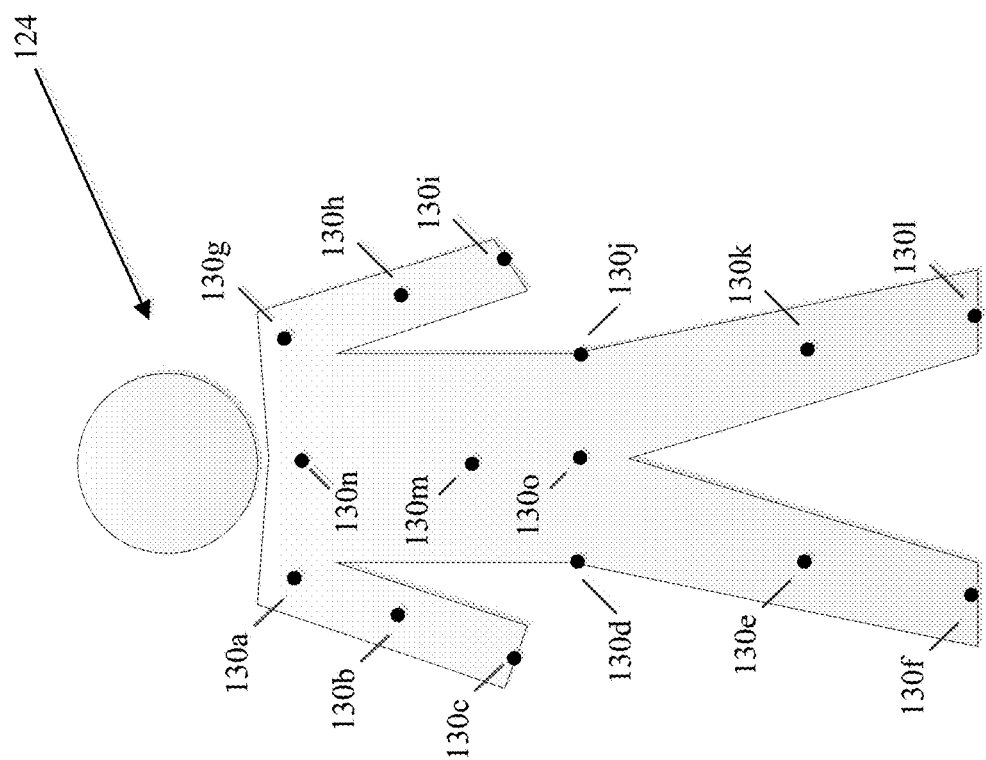
FIG. 5 shows illustrative locations for sensory input which may include physical sensors located on/in a user's clothing and/or be based upon identification of relationships between two moving body parts of the user.

FIG. 5 shows illustrative locations for sensory input (see, e.g., sensory locations 130a-130o). In this regard, sensors may be physical sensors located on/in a user's clothing, yet in other embodiments, sensor locations 130a-130o may be based upon identification of relationships between two moving body parts. For example, sensor location 130a may be determined by identifying motions of user 124 with an image-capturing device, such as image-capturing device 118. Thus, in certain embodiments, a sensor may not physically be located at a specific location (such as one or more of sensor locations 130a-130o), but is configured to sense properties of that location, such as with image-capturing device 118 or other sensor data gathered from other locations. In this regard, the overall shape or portion of a user's body may permit identification of certain body parts. Regardless of whether an image-capturing device is utilized and/or a physical sensor located on the user 124, and/or using data from other devices, (such as sensory system 302), device assembly 400 and/or any other device or sensor disclosed herein or known in the art is utilized, the sensors may sense a current location of a body part and/or track movement of the body part. In one embodiment, sensory data relating to location 130m may be utilized in a determination of the user's center of gravity (a.k.a, center of mass). For example, relationships between location 130a and location(s) 130f/130l with respect to one or more of location(s) 130m-130o may be utilized to determine if a user's center of gravity has been elevated along the vertical axis (such as during a jump) or if a user is attempting to "fake" a jump by bending and flexing their knees. In one embodiment, sensor location 1306n may be located at about the sternum of user 124. Likewise, sensor location 130o may be located approximate to the naval of user 124. In certain embodiments, data from sensor locations 130m-130o may be utilized (alone or in combination with other data) to determine the center of gravity for user 124. In further embodiments, relationships between multiple sensor locations, such as sensors 130m-130o, may be utilized in determining orientation of the user 124 and/or rotational forces, such as twisting of user's 124 torso. Further, one or more locations, such as location(s), may be utilized as (or approximate) a center of moment location. For example, in one embodiment, one or more of location(s) 130m-130o may serve as a point for a center of moment location of user 124. In another embodiment, one or more locations may serve as a center of moment of specific body parts or regions.

In this disclosure, various exemplary embodiments have been illustrated with running as the workout activity of choice. Those skilled in the art will realize that the scope of the disclosure pertains to various other exercising activities such as walking, bicycling, skateboarding, windsurfing, etc. all of which including numerous others not particularly mentioned are envisioned as being within the scope and spirit of the disclosure.

Figure 6:
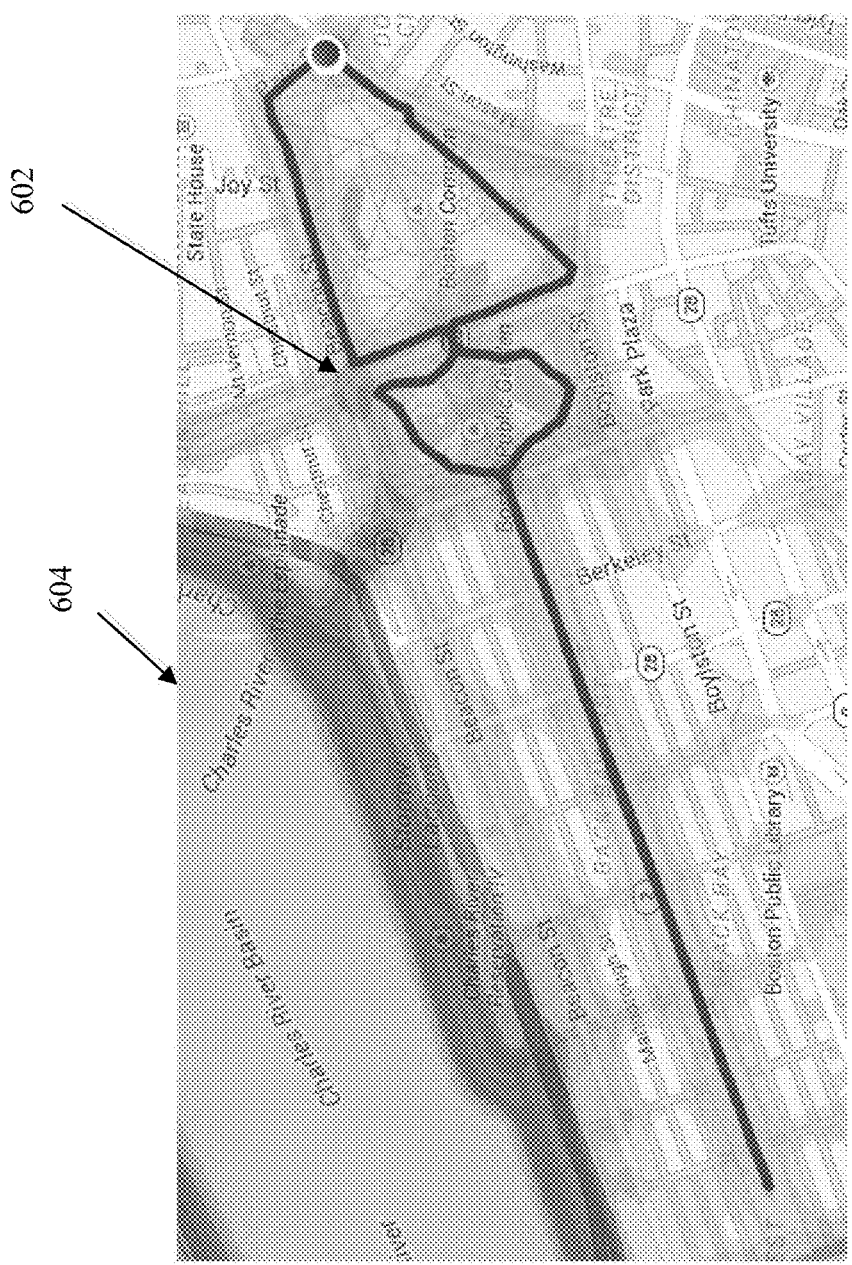
FIG. 6 illustrates an example interface including a map showing various locations along a top route in accordance with various aspects of the disclosure.
Figure 6A:
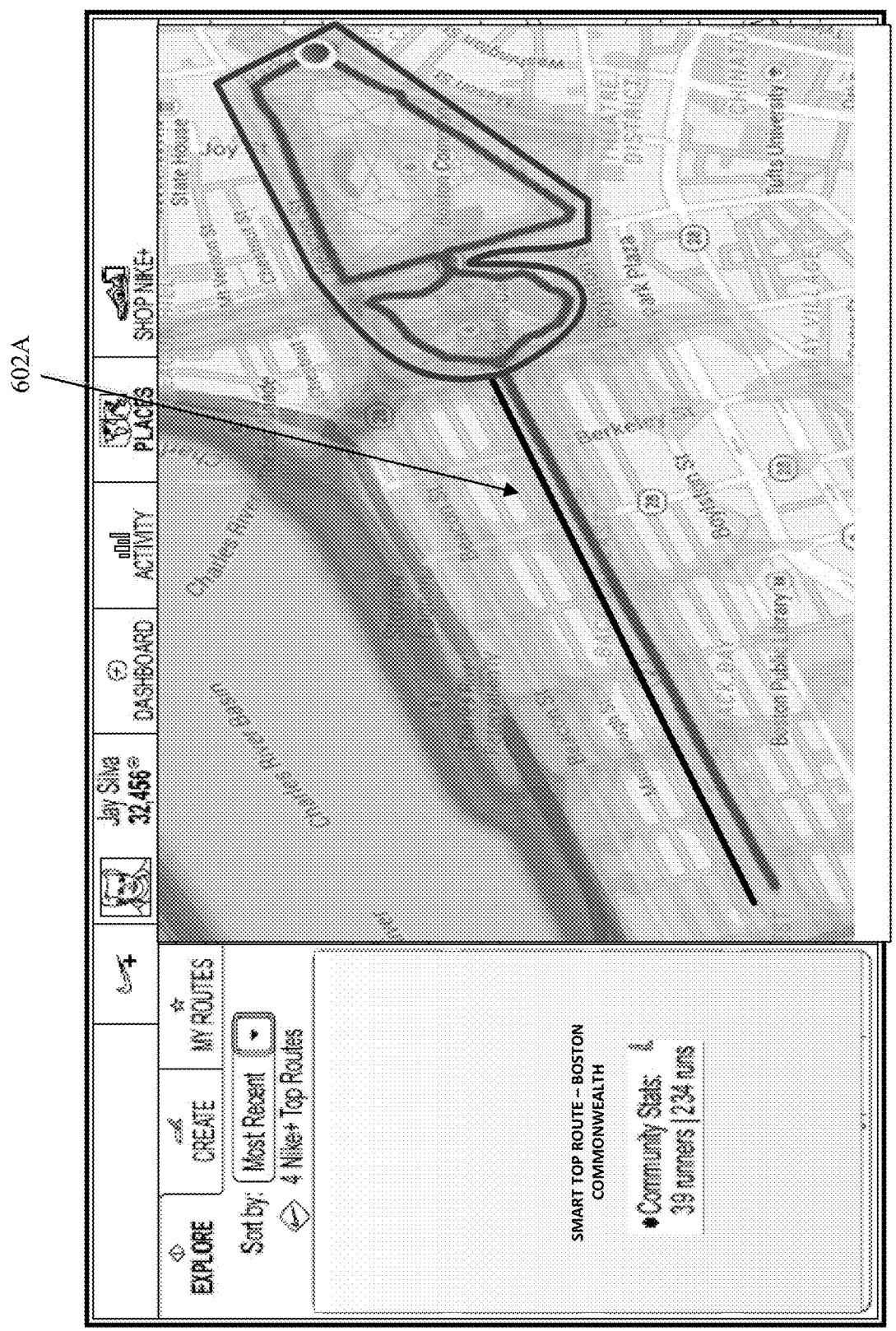

FIG. 6 illustrates an example interface including a map showing various locations along a top route in accordance with various embodiments of the disclosure. In an embodiment, a user such as user 124 arrives in a city such as Boston and decides that they wish to run a top route such as the top route referred to in Boston as the commonwealth top route 602. The commonwealth top route 602 may be displayed on user interface 604 on a mobile device such mobile device 114. User 124 not having been to Boston before needs directions and information regarding the commonwealth top route 602 such as how to get to the starting point of this top route. In addition, user 124 while running the common wealth top route 602 also needs to make sure he/she stays on course as they progress along this new route.

In an embodiment, a device such as smart top route activity tracking device 700 automatically directs user 124 from their location such as a hotel to the starting point of the commonwealth top route 602. In an embodiment, smart top route activity tracking device 700 may generate a smart top route 602A having enhanced functionally and user flexibility to that of the static top route 602.

In an embodiment smart top route 602A may provide navigation instruction's to user 124 in order for user 124 to safely arrive at the starting point for the commonwealth top route 602. For instance, smart top route activity tracking device 700 may provide real-time information based on construction, traffic reports, and safety events (e.g. Police Actions) and provide detours to user 124 or route alternatives for user 124 such that user 124 arrives at the commonwealth top route 602 quickly and safely.

In an embodiment, smart top route activity tracking device 700 may suggest based on heat maps and other real-time information the best time for user 124 to run the various top routes. In another embodiment, smart top route activity tracking device 700 may suggest to user 124 alternative smart top routes which it determines may be of interest to user 124. Such a determination may be made by smart top route activity tracking device 700 based on popularity of various top routes, time of day, running style of user 124, longer/shorter distances, more energy expenditure points, points of interest, scenic routes etc.

In an embodiment, a user's progress along a smart top route may be tracked in real-time and stored. During the workout, smart top route activity tracking device 700 may suggest to user 124 variations of the top route based on a user's measured performance on various portions of a top route. The alternative smart top routes may increase or decrease the intensity of the overall workout session. Such alternative smart top routes suggestions may include grade or elevation changes to make the workout more difficult and assist user 124 in obtaining workout goals for the workout session. Such alternative smart top routes determinations may be offered to user 124 to further motivate user 124 and take into account information such as heart rate monitoring, distance, pace, energy expenditure points or score, along with other workout statistics.

Figure 7:
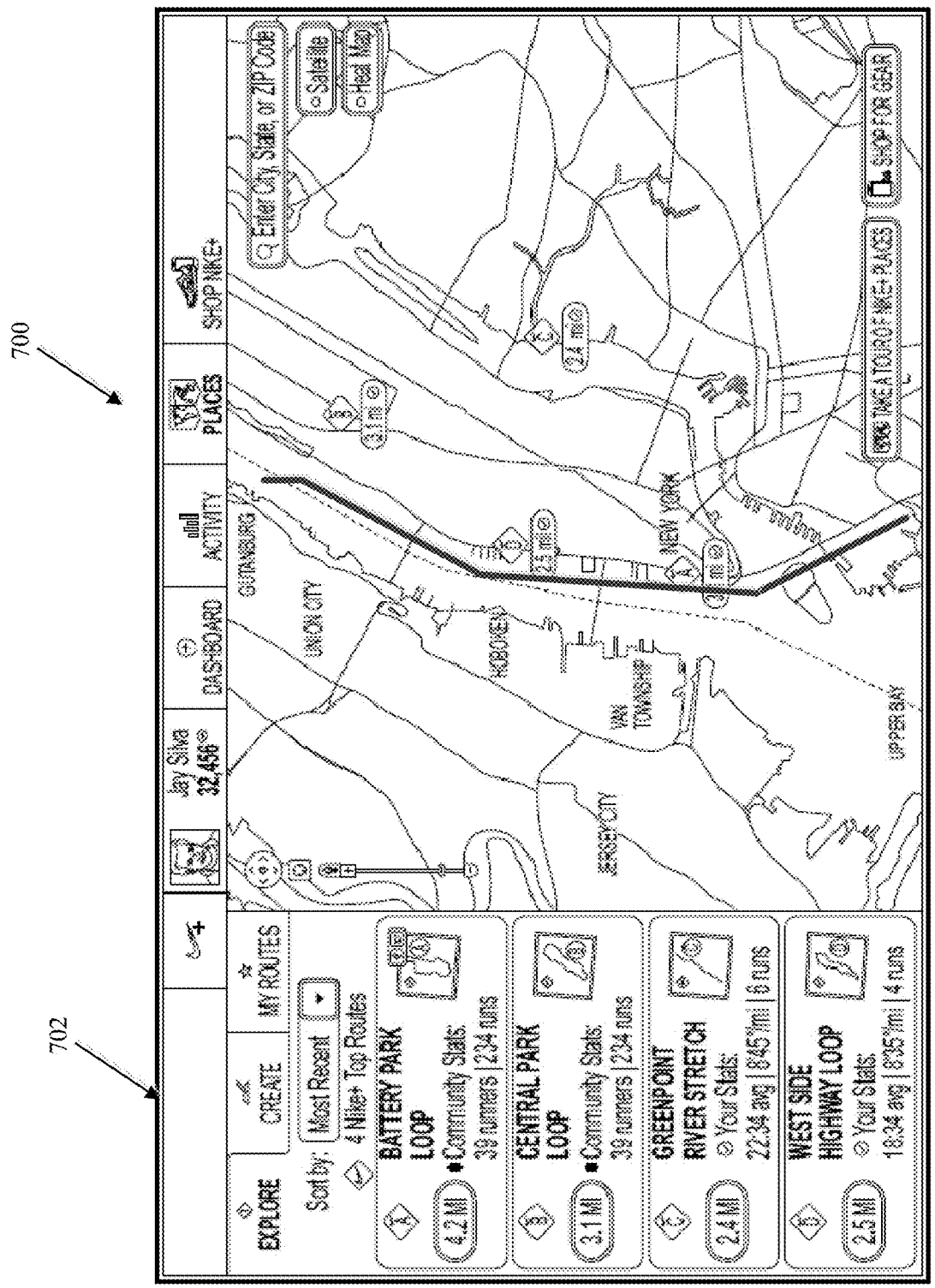

In another embodiment, smart top route activity tracking device 700 may further provide the ability for user 124 to track progress along different smart top routes or activity routes. For example, FIG. 7 illustrates an example interface 702 including a map showing various locations where smart top routes or other activity routes have been defined. The smart top routes or activity routes may be represented on the map by a visual element that may include a visual feature indicating whether user 124 has completed that top route before. Additionally, an information bar may display detailed information about each of the various smart top routes or activity routes and provide user statistics (e.g., for best run or a most recent run) if user 124 has previously completed or ran that top route. A best run may be defined in terms of a lowest or highest metric (e.g., highest calories burned, lowest pace, longest distance, etc.).

In an embodiment, user statistics might correspond to cumulative statistics for all performances by the user for that top route or activity route. If a user has not previously run the top route or activity route (or has not used the top route or activity route for a predefined amount of time), the information bar may display instead statistics for one or more other individuals that have performed the top route or activity route.

While the interface 702 only shows one area of the world, the user may also search for other areas of the world using a search field. In addition, interface 702 which may use GPS location functionality may display the closest smart top routes or activity routes within a user defined circumference. The interface, in one or more examples, might only show areas in which smart top routes have been defined. Additionally or alternatively, a user may be able to filter the smart top routes or activity routes shown in the map using a variety of parameters. For example, a user may filter the smart top routes or activity routes by popularity level and/or activity level. Popularity may be defined in a variety of ways including based on a number of times the top route has been used, a number of positive comments or votes received, a number of times the top route has been shared and the like. In yet another example, a user may filter the smart top routes or activity routes based on difficulty level. Difficulty level may be defined by a creator of the smart top route or activity route or may be defined by votes/tags submitted by users who have previously used the smart top route or activity route. Difficulty level may also be defined based on metrics measured from that smart top route or activity route. For example, if the average heart rate for multiple users who have used the smart top route or activity route is above a specified threshold, the smart top route or activity route may be scored with high difficulty. Accordingly, different difficulty levels may correspond to different heart rate ranges. Other filtering parameters may include distances, estimated or average actual amount of time required, number of friends or other users who have performed the smart top route or activity route and the like.

In some instances, the interface may automatically filter out smart top routes or activity routes based on a user's workout history and/or other characteristics. For example, if a user's longest run was 10 miles, the interface may filter out smart top routes or activity routes that are greater or less than the user's longest run by a predefined amount (e.g., 30%, 50%, 75%, 100%, etc.). In other examples, if a user has indicated a dislike of mountain running or trail running, the system may automatically filter out such smart top routes or activity routes. In yet another example, the interface may filter by time of day, locations, safety, popularity of route (i.e. how often the route is run, and/or how crowded of an area or popular the street/trail may be) it is during that time of day. Various other rules and automatic filters may be specified and applied as desired by the user.

In another embodiment, the smart top route activity tracking device 700 may enable a user to join a running club (i.e. Nike running club) at various points along a smart top route. Such points may be indicated on the smart top route. In addition, a user may join a running club even if the user is late to the scheduled run. In an embodiment, the smart route may allow a late user to join a running club and enable them to participate placing them on the smart route at a point that would be equivalent to "where the average of the running club is located". This would allow users to join at any time and feel good about being part of the running community.

Figure 8:
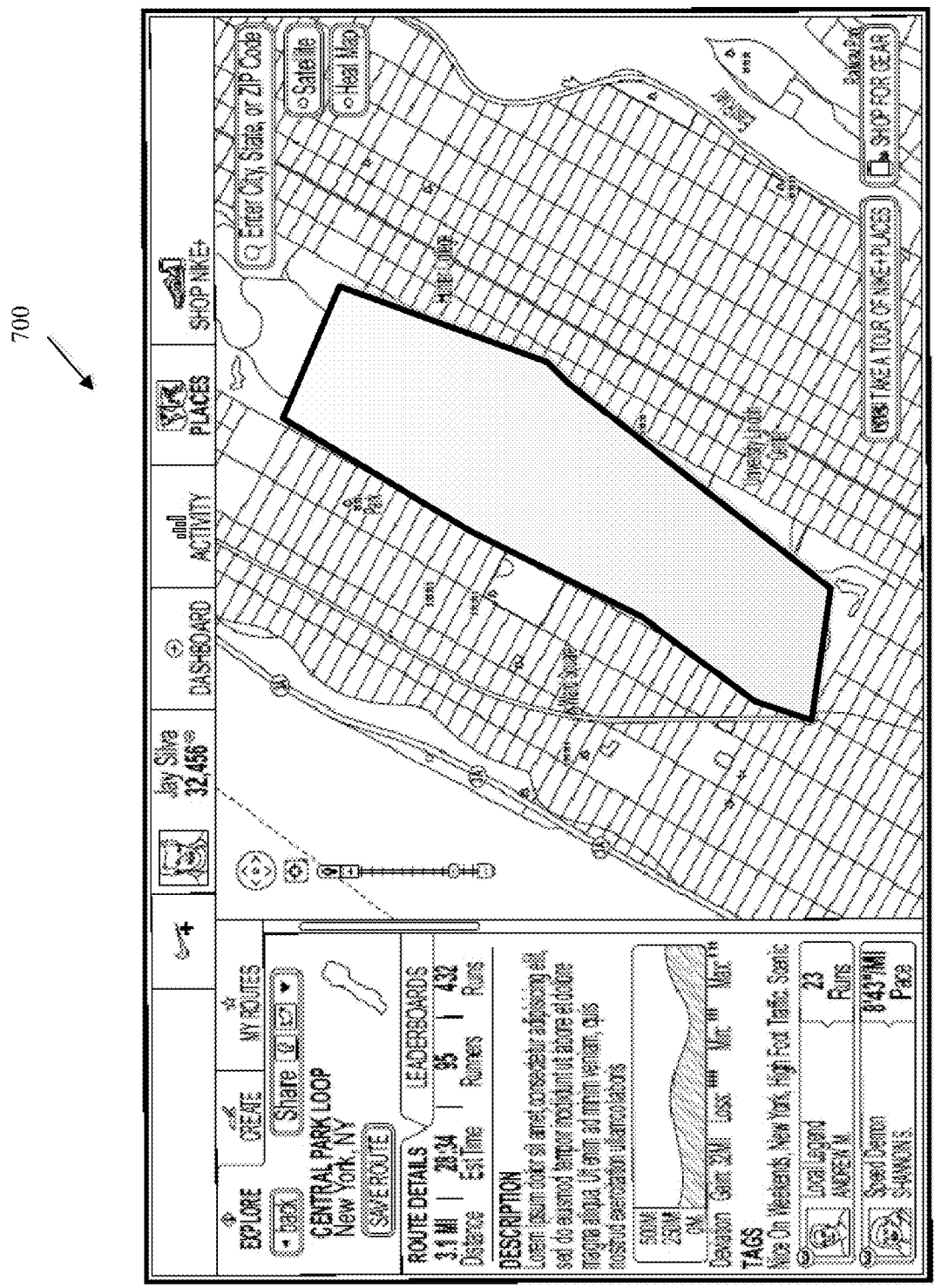
Figure 9:
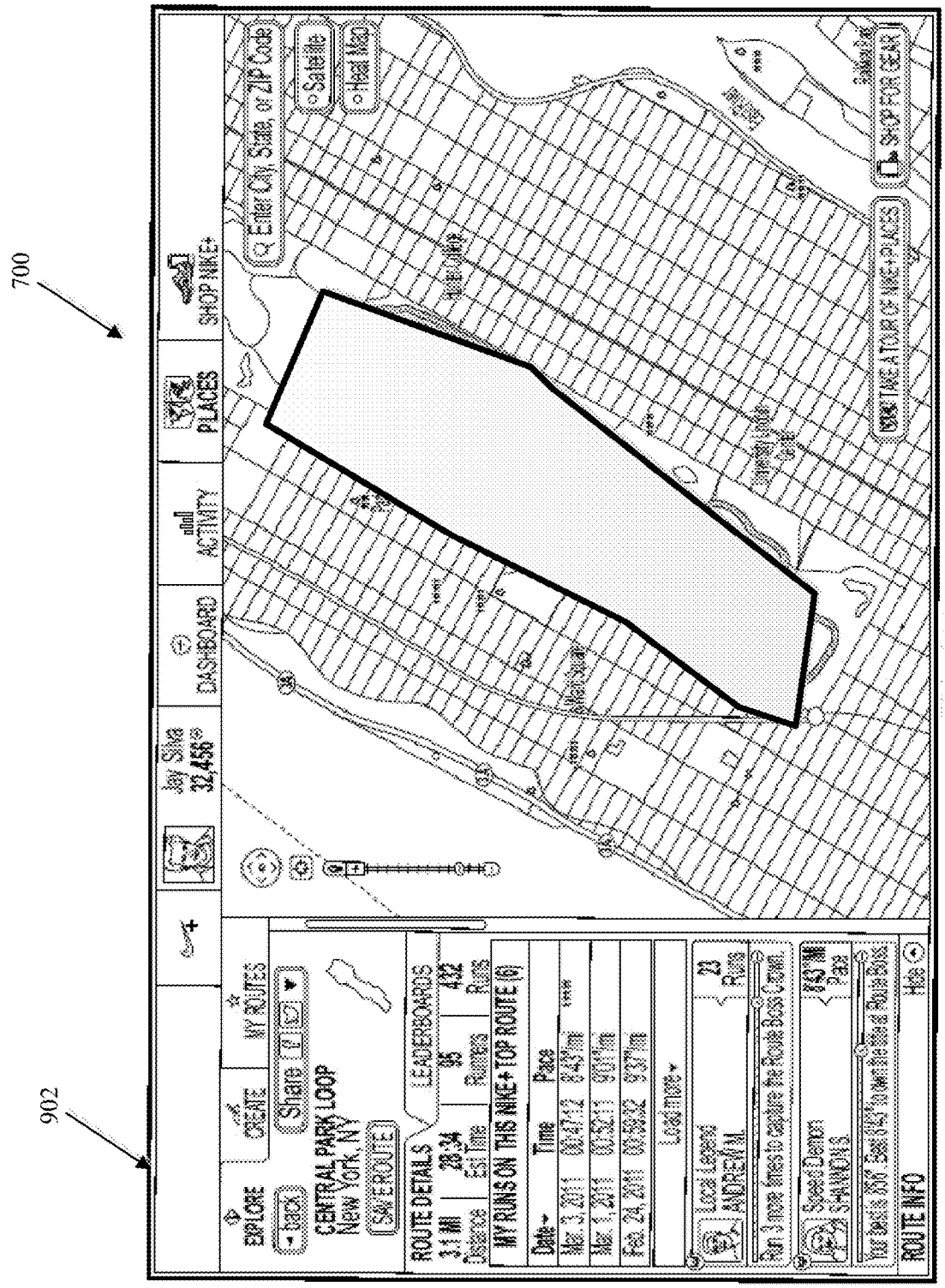

FIGS. 7-9 illustrate interfaces in which smart top route details are displayed. For example, if a user selects one of the smart top routes or activity routes displayed in the information bar or on the map in FIG. 7, the user may be directed to a user interface such as those shown in FIGS. 7-9.

In FIG. 8, for example, displays the smart top route of a run in the map and details of the route in the information bar. In particular, information bar may provide details such as a length of the run, an estimated amount of time required for the run, a number of users that have performed the run, a number of runs performed and the like. An elevation graph may also be provided to indicate the elevation changes that are involved during the run. A description (e.g., creator defined) of the route may also be displayed. In one or more examples, the route may also be tagged with various key words submitted by users. These key words or tags may aid in searching for routes that fit a user's interest, athletic level and/or needs. The information bar may further display one or more runners that have run the route. For example, the information bar may display the fastest runner for the route as well as the runner who has run the route the most number of times along with their relevant metrics. This information may provide the user with added motivation to try to reach the top position with respect to a number of time run or fastest pace. In other examples, a system may randomly select users to display in the route details.

According to some aspects, information displayed in the information bar and/or the map may be interactive. For example, if a user hovers over or otherwise interacts with a particular segment of the elevation map, a corresponding portion of the route displayed in the map may be highlighted or otherwise indicated (e.g., a label, pointer, icon, etc.). In yet other examples, a user may hover over or otherwise interact with a portion of the route displayed in the map to cause a pop-up display to show a best or average pace at that point in the route. Additionally or alternatively, images, photographs, notes and the like provided by users may also be displayed upon interacting with a portion of the route.

FIG. 9 illustrates an example interface 902 that may be displayed when a user has previously run the smart top route one or more times. The interface may display metrics for one or more previous runs. The previous run information may be sorted or selected based on the best previous runs according to one or more metrics such as pace. The information bar, in addition to identifying the leaders in various categories for the route, may further display a comparison between the current user and the leaders. Accordingly, the user may be provided information such as a number of runs needed to exceed the current number of runs leader or a pace gap between the user and the pace leader for the route. This information may provide additional motivation to challenge the user.

Figure 10:
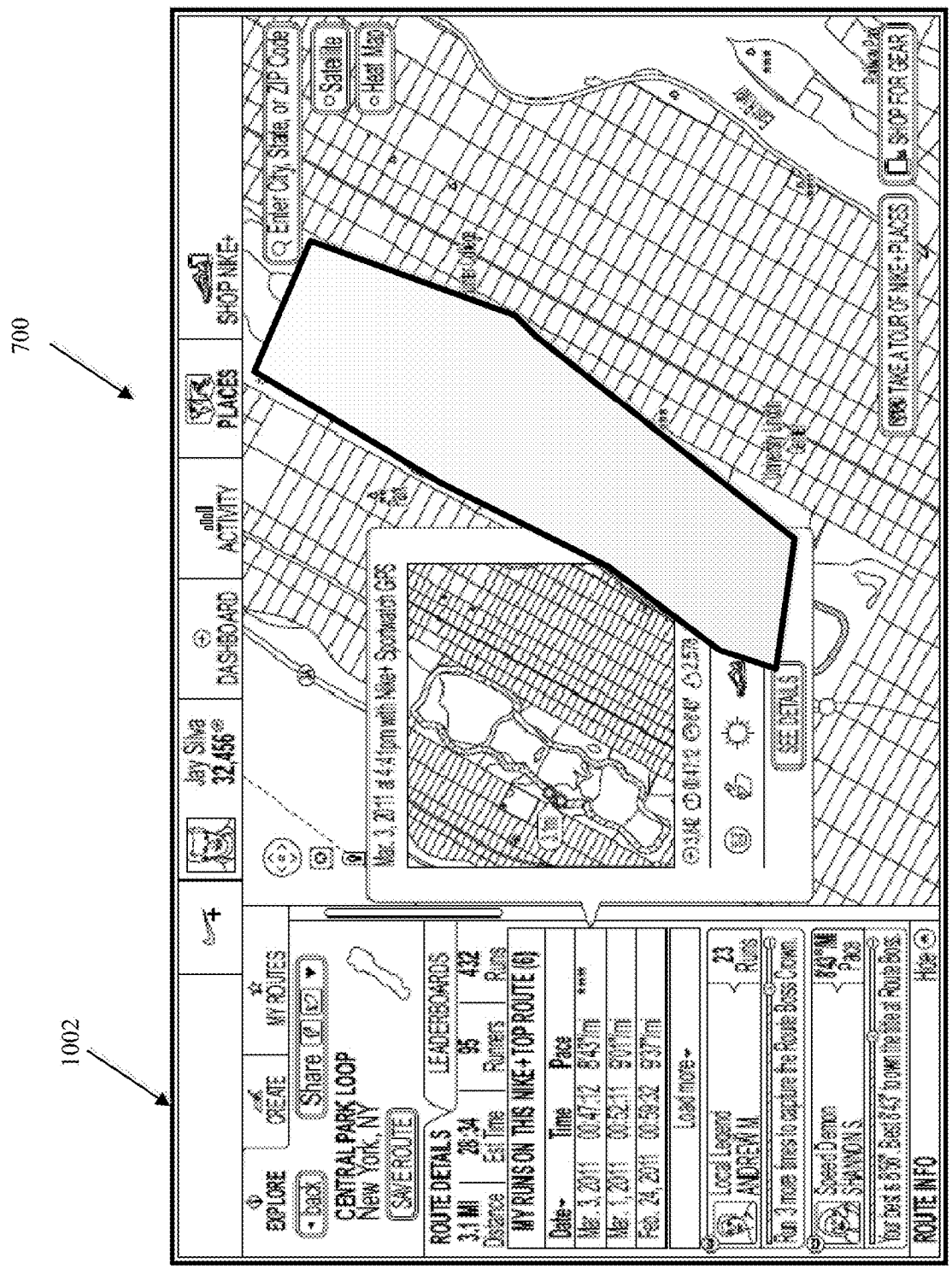

FIG. 10 illustrates an interface 1002 in which a sub-interface is displayed upon selection or other interaction with one of the user's previous runs. The sub-interface may provide additional details regarding the previous run including a device with which the run was measured, metrics of the run, and tags associated with the run (e.g., weather, mood, terrain and equipment used). Additionally, the sub-interface may provide an image of the route with an indication of a particular metric of the user during the run. For example, the appearance of the route may be defined based on a heart rate or pace of the user at the corresponding points of the run. According to another example, selecting a particular run may cause the route displayed in the main interface map to change to a metric-indicative route line.

Figure 11:
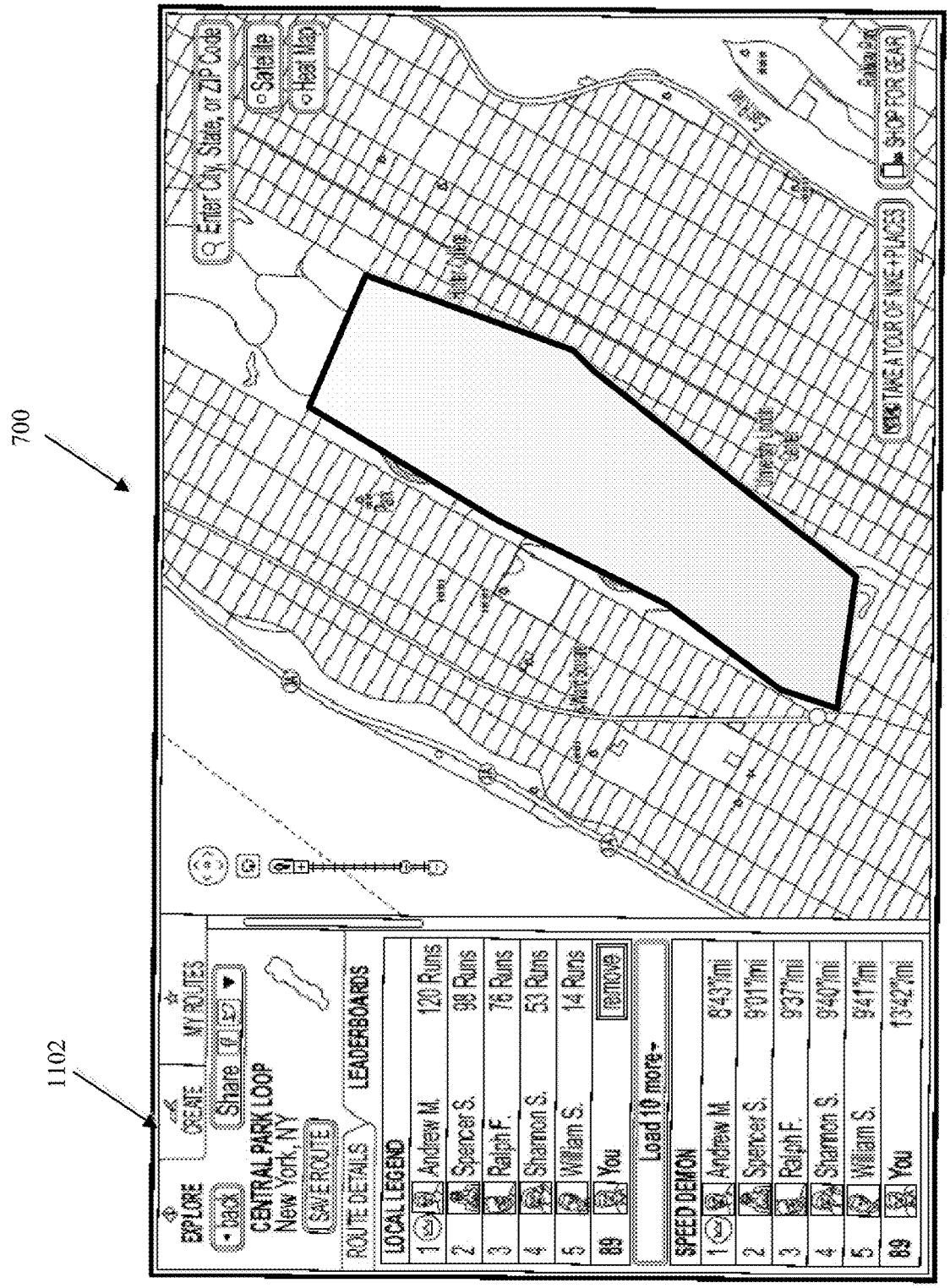

FIG. 11 illustrates another example interface 1102 showing a smart top route and an information bar. The information bar displays a leaderboard of individuals for each of number of times run and speed/pace. The current user may always be displayed in the leaderboard regardless of their position. The user may also have the option of removing themselves from the leaderboard. Removal from the leaderboard may include removing records of the runs associated with the route. Alternatively, removal from the leaderboard might only include disassociation of the run records with the particular route. For example, the run metrics (e.g., distance, pace, etc.) might still be recorded in the user's overall running history and accumulated totals and averages. In other examples, removal may include hiding the record from the public. Accordingly, while the record may still be linked to the route when the user views the recorded run, the association might not be viewable to others.

Figure 12:
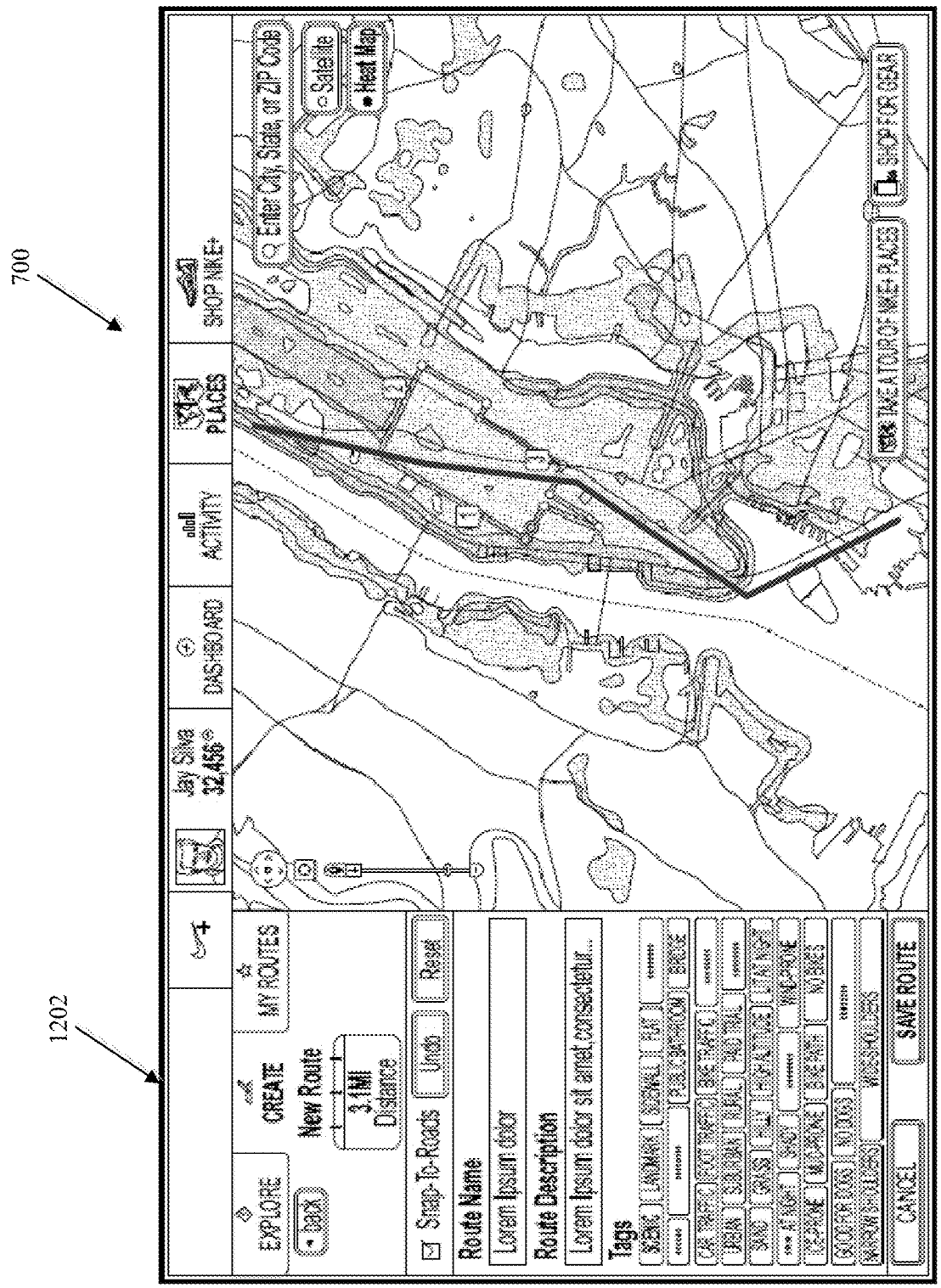

FIG. 12 illustrates a smart top route creation interface 1202. Smart top route creation interface 1202 may allow a user to manually draw a path in the map to represent a route that is to be run. In other examples, a user may upload a route (e.g., recorded using GPS) that they have previously run and modify the route as desired. In defining the route, the user may enter a name, provide a route description and tag the route with one or more key words or phrases.

Additionally, the smart top route display may include a heat map. The use of the heat map is not limited to route creation and may be displayed in other environments including reviewing of a user's performance and viewing available routes. The heat map may represent a level of popularity or activity for the corresponding areas of the map. The heat map may be specific to athletic activity and thus, might not include information regarding other activity that is performed in those areas. In some examples, the heat map may be configured to be specific to (e.g., only reflect data for) one or more particular types of athletic activities, activity recorded using one or more particular types of devices, one or more demographic groups, and the like and/or combinations thereof. The heat map may specify the level of activity or popularity by using varying colors or shades of colors, patterns, transparencies or other varying visual appearance. For example, a dark red color may represent high levels of activity or popularity while a lighter red color (e.g., pink) may represent low levels of activity or popularity in the corresponding area. Hovering over an area of the map may provide additional information such as a number of runs performed per day or other time period, a number of distinct runners that run in the area per day or per week or other time period, a most recent run in the area and the like. The heat map may be activated or deactivated as desired. For example, a user may return to a normal line-map or activate a satellite-map.

In one or more examples, the system may automatically generate a smart top route based on a user specified distance, a user specified amount of time, general location (e.g., city, zip code, neighborhood, address, etc.) and/or information from a heat map. The device may generate the smart top route by maximizing the popularity or activity level of the areas through which the route extends. In one example, a user may specify a start location and an end location and the device may automatically determine a smart top route that maximizes popularity or activity level based on previously stored activity information. Alternatively, the device may generate a smart top route that minimizes the popularity or activity level of the areas through which the route extends. Whether the activity level/popularity level is maximized or minimized may be user selectable. In one or more arrangements, generating the smart top route based on a user specified amount of workout time may include analyzing a popularity or activity level of potential routes. For example, routes with higher popularity or activity level may require more time to traverse. Accordingly, the smart top route may be shortened (e.g., relative to a route through less popular areas or areas with lower activity levels) to meet the specified amount of workout time.

Figure 13:
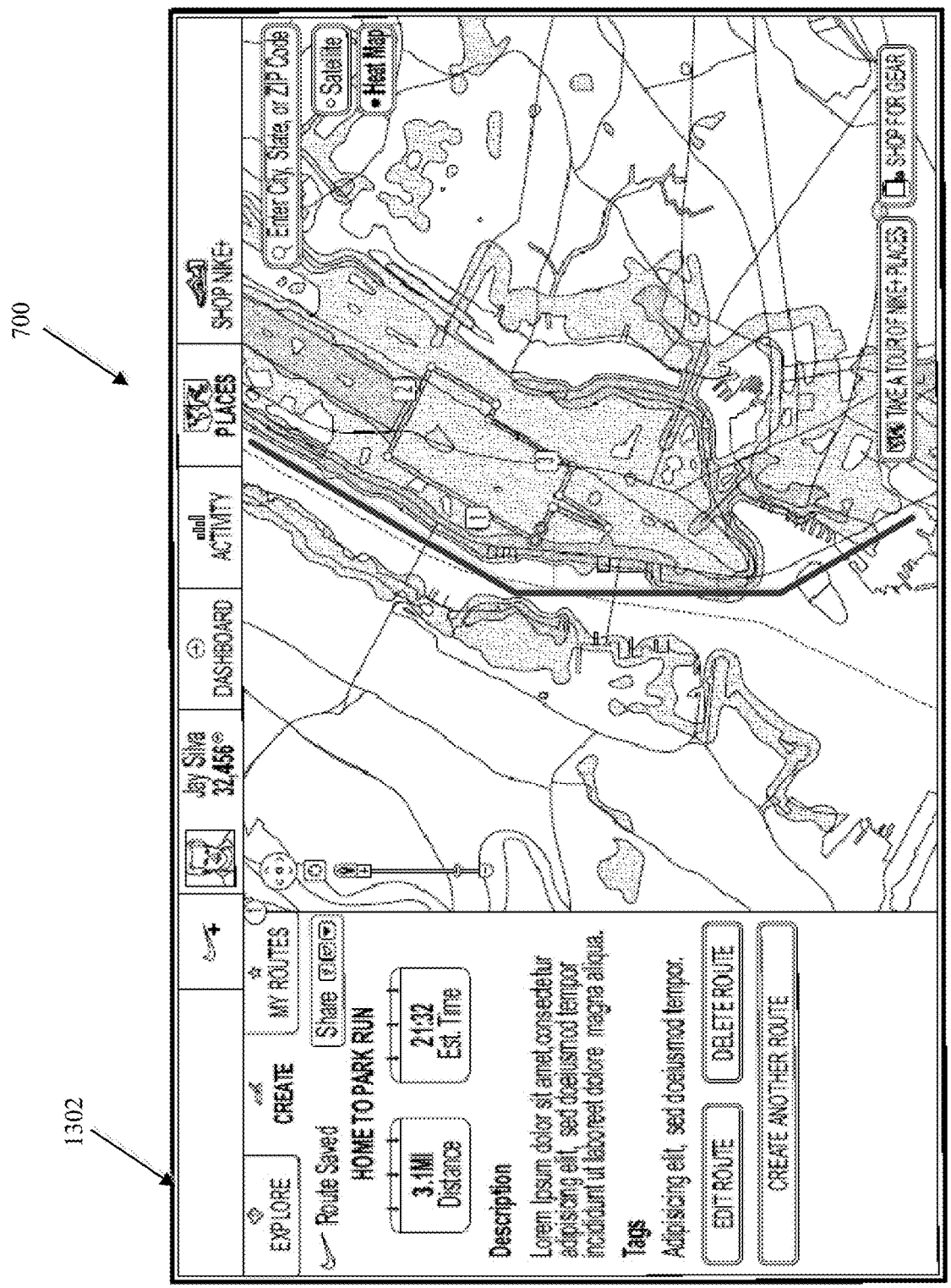

FIG. 13 illustrates another example smart top route creation interface 1302 in which an estimated time to complete is displayed. The estimated time to complete may be calculated based on a user's average pace (total or for similar terrain, length and/or elevation).

In an embodiment, smart top route activity tracking device 700 may integrate route matching directly into the smart top route activity tracking device 700 to provide user 124 with accessible and reliable smart top route information. In embodiment, a fuzzy match may be used to determine candidate smart top routes for various workout activities. In an aspect of the disclosure, a route match may be completed if a fuzzy match indicates a likelihood of actual route match.

In an embodiment, a complete route match or full route match may only be completed if the fuzzy match indicates a sufficient likelihood of an actual route match. In an embodiment, the full route match includes intersecting the run geometry with the route geometry to determine a sufficient match.

In an aspect of the disclosure, a fast lookup mechanism using a fuzzy match may be implemented given a set of waypoints. If a run sufficiently matches a route then a match percentage may be calculated and stored with a route identification number.

In yet another embodiment, a fast lookup for the identified smart top routes maybe generating a dictionary of smart top routes. The dictionary of smart top routes may be sorted based on each route's Euclidean distance from (0,0) longitude/latitude (i.e. intersection of equator and prime meridian).

In an embodiment for all smart top routes smart top route activity tracking device 700 may:
Compute Geo-Centroid: the point defined by the arithmetic mean of x and y coordinates
Compute the radial coordinates (r,Θ) "RC" for this route's Geo-Centroid
Add entry for {(r,Θ): Top Route ID} to the Top Route dictionary
Sort Top Route lookup by the (r,Θ)-key In an embodiment, smart top route activity tracking device 700 may execute a search that determines whether a fuzzy match exists between a candidate run and a top route set:
Accepts a Geo-Centroid argument, and a maxDistanceForMatch argument
    Could also accept all waypoints for a Run and encapsulate computation of the Geo-Centroid in a utility method
    Could also encapsulate any filtering of input waypoints in a utility method
Computes (r,Θ) for Run Geo-Centroid
Binary search through Top Route lookup by (r,Θ)-key
    Compute Euclidean distance between closest Top Route centroid and passed centroid
    Remember the RouteId with smallest Euclidean distance
If smallest distance is less than or equal to the maxDistanceForMatch, return matched routeId, else return no match
    Note: If at any point multiple matches should be returned, then we would augment this method to return a list of routeIds that qualify.

In an aspect of the disclosure, routes surfaces and run waypoints may be sorted or filtered by their longitude values, prior to comparison. This may allow a single quick calculation to determine if the run waypoint is within the longitude range of the next surface. The calculation may allow either the run waypoint or the route surface to be discarded if outside the required range.

Aspects of the embodiments have been described in terms of illustrative embodiments thereof. Numerous other embodiments, modifications and variations within the scope and spirit of the appended claims will occur to persons of ordinary skill in the art from a review of this disclosure.

The invention claimed is:

1. A method comprising:
receiving, by a computing device, athletic activity data generated by one or more sensors associated with each of a plurality of athletes, wherein the one or more sensors are used to determine a location for each of the plurality of athletes;
generating, by the computing device and based on the athletic activity data, a user interface indicating a map and information regarding athletic activity performed by the plurality of athletes in an area displayed in the map;
receiving, by the computing device, a workout time period and distance parameters;
generating, based on the received workout time period and distance parameters, a first route to be traversed by a user;
determining, by the computing device and using location information obtained from the one or more sensors, an average location, in the area displayed in the map, of a first group of athletes traversing a second route;
generating, by the computing device and based on the average location of the first group of athletes, routing information directing the user to one or more points along the second route during a first time period such that the user may join the first group of athletes traversing the second route; and
displaying, via the user interface, the routing information or joining the first group of athletes traversing the second route.

2. The method of claim 1, further comprising generating a third route extending through a first sub-area and a second sub-area, of the area displayed in the map, wherein generating the third route includes selecting the first sub-area and the second sub-area to maximize an overall workout intensity level.

3. The method of claim 1, further comprising:
detecting that the user is interacting with a first portion of the user interface; and
in response to the detecting, generating, based on a location of the first portion, a sub-interface displaying athletic activity metrics associated with the first route.

4. The method of claim 1, wherein generating the user interface includes generating one or more heat maps.

5. The method of claim 1, wherein generating the first route further includes selecting one or more sub-areas, of the area displayed in the map, based on activity level on the first route.

6. The method of claim 1, wherein generating the first route further includes selecting one or more sub-areas, of the area displayed in the map, based on popularity level of the first route.

7. The method of claim 1, wherein the determined location comprises an average location of the one or more of the plurality of athletes along the second route.

8. A method comprising:
receiving, by a computing device, athletic activity data generated by one or more sensors associated with each of a plurality of athletes, wherein the one or more sensors are used to determine a location for each of the plurality of athletes;
generating, by the computing device and based on the athletic activity data, a user interface indicating a map and information regarding athletic activity performed by the plurality of athletes in an area displayed in the map;
determining, by the computing device and using location information obtained from the one or more sensors, an average location, in the area displayed in the map, of the plurality of athletes traversing a first route;
generating, via the user interface and based on the determined location, routing information enabling a user to join the plurality of athletes traversing the first route during a first time period; and
outputting for display, via the user interface and based on the average location, an indication of where along the first route the user will join the plurality of athletes.

9. The method of claim 8, wherein the routing information includes global positioning system (GPS) directional data.

10. The method of claim 8, further comprising generating a second route based on a remaining workout time period, the second route extending through one or more sub-areas in the area displayed in the map.

11. The method of claim 8, further comprising:
receiving, by the computing device, user input indicating one or more distance parameters; and
generating, by the computing device, a second route based on the one or more distance parameters, the second route extending through one or more sub-areas in the area displayed in the map.

12. The method of claim 11, wherein generating the second route further includes selecting the one or more sub-areas based on activity level on the second route.

13. The method of claim 11, wherein generating the second route further includes selecting the one or more sub-areas based on a popularity level of the second route.

14. The method of claim 8, further comprising generating a second route extending through a first sub-area and a second sub-area displayed in the map, wherein generating the second route includes selecting the first sub-area and the second sub-area to maximize an overall workout intensity level.

15. The method of claim 8, further comprising generating a second route extending through a first sub-area and a second sub-area displayed in the map, wherein generating the second route includes selecting the first sub-area and the second sub-area to minimize an overall workout intensity level.

16. The method of claim 8, wherein generating the user interface includes generating one or more heat maps.

17. An apparatus, comprising:
one or more processors;
a location-determining sensor configured to determine location data using global positioning system (GPS) functionality;
a media content interface; and
a non-transitory computer-readable medium storing computer-executable instructions, wherein the computer-readable medium further comprises computer-executable instructions that, when executed by the one or more processors, cause the apparatus to perform at least:
receiving athletic activity data for a plurality of athletes;
generating, based on the athletic activity data, a user interface indicating a map and information regarding athletic activity performed by the plurality of athletes in an area displayed in the map;
generating, based on an average location of the plurality of athletes traversing a first route, routing information enabling a user to join the plurality of athletes traversing the first route during a first time period; and displaying, via the user interface, the routing information.

18. The apparatus of claim 17, wherein the apparatus is configured to be worn on an appendage of the user.

19. The apparatus of claim 17, wherein the computer-readable medium further comprises computer-executable instructions that, when executed by the one or more processors, cause the apparatus to perform at least:

generating a second route based on a remaining workout time period, the second route extending through one or more sub-areas of the area displayed in the map.

20. The apparatus of claim 17, wherein the computer-readable medium further comprises computer-executable instructions that, when executed by the one or more processors, cause the apparatus to perform at least:

generating a second route extending through a first sub-area and a second sub-area displayed in the map, wherein generating the second route includes selecting the first sub-area and the second sub-area to maximize an overall workout intensity level.

* * * * *